US00PP29364P3

(12) United States Plant Patent
Fourie

(10) Patent No.: US PP29,364 P3
(45) Date of Patent: Jun. 12, 2018

(54) APPLE TREE NAMED 'STARAPPLE1'

(50) Latin Name: ***Malus domestica* Mills**
Varietal Denomination: Starapple1

(71) Applicant: STARGROW CULTIVAR DEVELOPMENT (PROPRIETARY) LIMITED, Stellenbosch (ZA)

(72) Inventor: Jeanne Fourie, Stellenbosch (ZA)

(73) Assignee: Stargrow Cultivar Development (Proprietary) Ltd., Stellenbosch (ZA)

( * ) Notice: Subject to any disclaimer, the term of this patent is extended or adjusted under 35 U.S.C. 154(b) by 6 days.

(21) Appl. No.: 15/330,026

(22) Filed: Jul. 27, 2016

(65) Prior Publication Data

US 2018/0035585 P1 Feb. 1, 2018

(51) Int. Cl.
*A01H 5/08* (2018.01)

(52) U.S. Cl.
USPC ..... Plt./161
CPC ..... *A01H 5/0875* (2013.01)

(58) Field of Classification Search
USPC ..... Plt./161
CPC ..... A01H 5/0875
See application file for complete search history.

(56) References Cited

PUBLICATIONS

South African Plant Variety Journal; http://www.daff.gov.za/docs/variety/PVJ_127.pdf; Jul. 2010 to Sep. 2010; 12 pages.*

* cited by examiner

*Primary Examiner* — Kent L Bell
(74) *Attorney, Agent, or Firm* — Kilpatrick Townsend & Stockton LLP

(57) ABSTRACT

'Starapple1' is new apple tree variety that in combination can be distinguished from other apple varieties by its percentage and intensity of red over-color; intense flavor with high sugar:acid ratio and balanced eating quality; red "bleeding" into the flesh at harvest; and scab resistance.

3 Drawing Sheets

Genus and species: The apple tree variety of this invention is botanically identified as *Malus domestica* Mills.

Variety denomination: The variety denomination is 'Starapple1'.

BACKGROUND OF THE INVENTION

The invention refers to a new and distinct plant variety of apple tree (*Malus domestica*) named 'Starapple1'. The new *Malus* variety is a product of a planned and controlled breeding program for new *Malus* varieties. The objective of the breeding program is to select new *Malus* varieties with improved characteristics in color development, eating quality, production and disease resistance.

The new *Malus* variety was obtained through an open pollinated cross of which the female parent is unknown. Seedlings of the population were top grafted on existing rootstocks. The first fruit of 'Starapple1' was observed in February 2005 from the top-grafted tree. Buds where selected from the top-grafted trees and 5 trees were propagated on M793 rootstock as second generation trees. No comparison between the seedling and the parents could be performed due to the fact that the parents are unknown. Fruit from the second generation trees was first observed in 2008. 'Starapple1' was selected in 2009 after the second fruit crop from the second generation trees for further development because of the unique fruit quality traits observed over the two seasons consecutively.

BRIEF SUMMARY OF THE INVENTION

The following traits have been repeatedly observed and are determined to be unique characteristics of 'Starapple1' which in combination distinguish this apple tree as a new and distinct variety:

1. Percentage and intensity of red over-color;
2. Intense flavor with high sugar:acid ratio and balanced eating quality;
3. Red "bleeding" into the flesh at harvest; and
4. Scab resistance.

The fruit of 'Starapple1' ripens between 'Gala' and 'Golden Delicious'. Compared to 'Gala', fruit of 'Starapple1' develops a darker red over-color and has a significantly different flavor with a higher sugar:acid ratio. Compared to 'Golden Delicious', fruit of 'Starapple1' ripens one week earlier and has a nearly full dark red over color where 'Golden Delicious' fruit has a greenish-yellow over color at harvest.

Fruit of 'Starapple1' develops a unique high intensity red over-color at harvest with some strippiness on the shaded side of the fruit. Fruit of 'Starapple1' develops a unique color intensity compared to other apple varieties ripening during the same period. When ripe, some fruit shows strong red "bleeding" into the flesh from the skin, giving 'Starapple1' a distinguishable flesh appearance.

BRIEF DESCRIPTION OF THE PHOTOGRAPHS

The accompanying photographs illustrate the appearance of the new apple tree in production, fruit and internal quality of the fruit. The color of the photographs might vary slightly compared to the variety description, however the botanical description is the more accurate description of the true color of this new variety.

Figure 1:
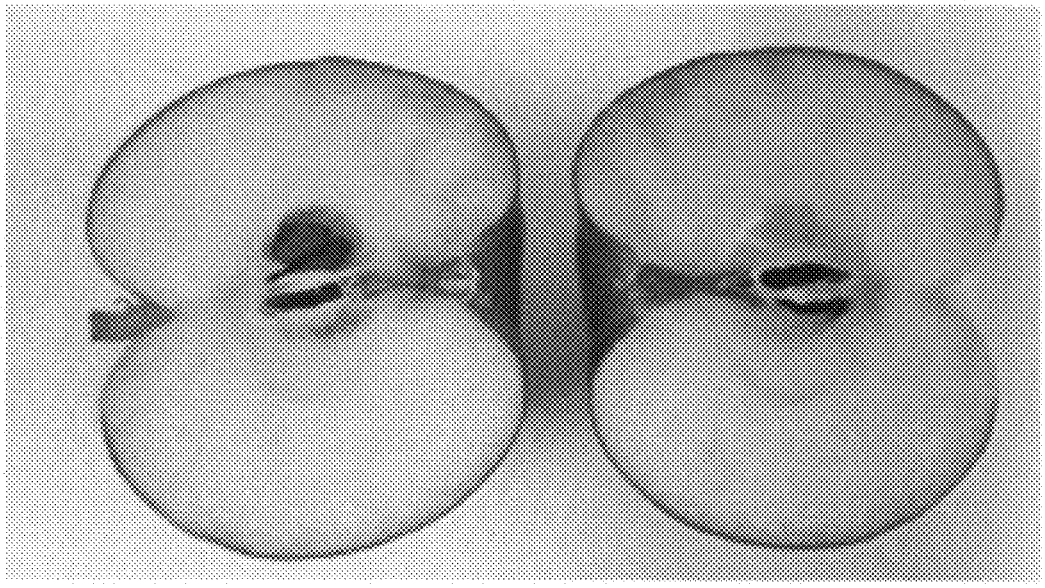

FIG. 1. Photograph of a central axis cut of fruit showing the flesh color with contrasting bleeding into the flesh close to the skin.

Figure 2:
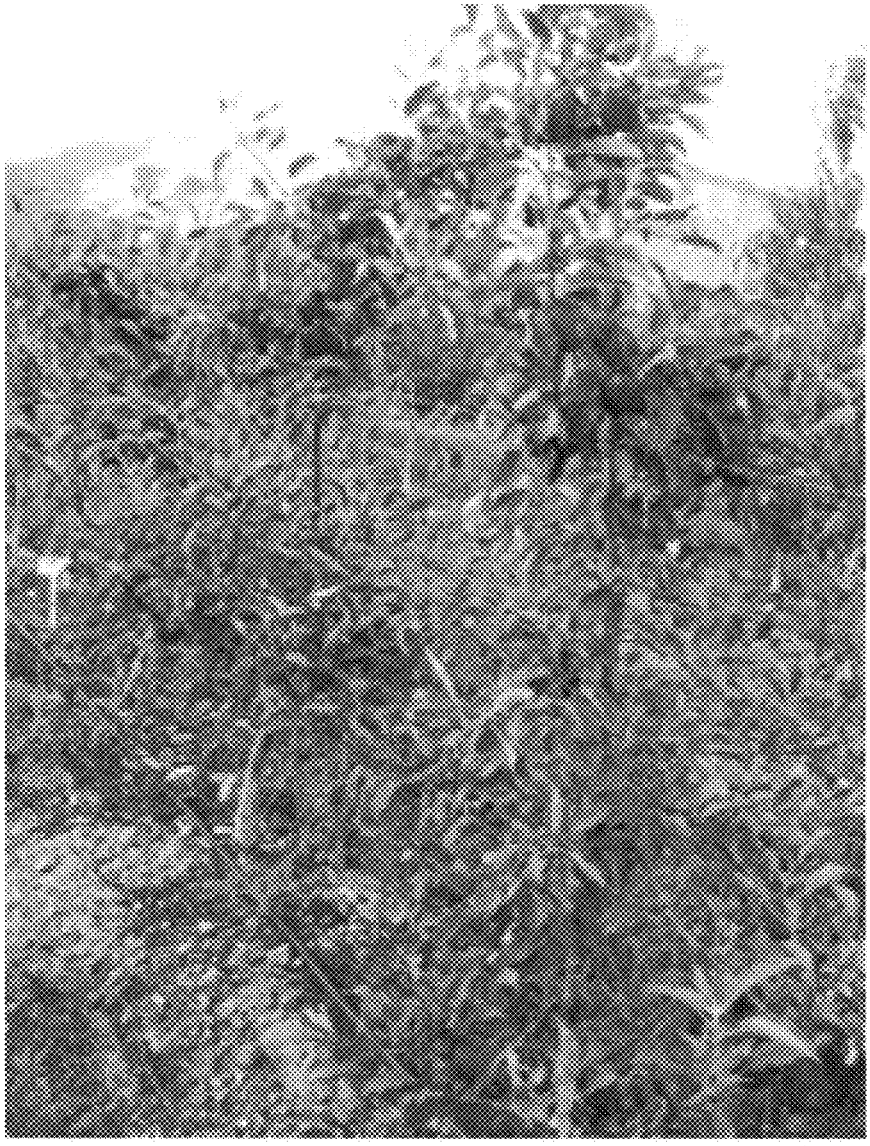

FIG. 2. Photograph showing a tree of this new variety, typically in production in an orchard.

Figure 3:
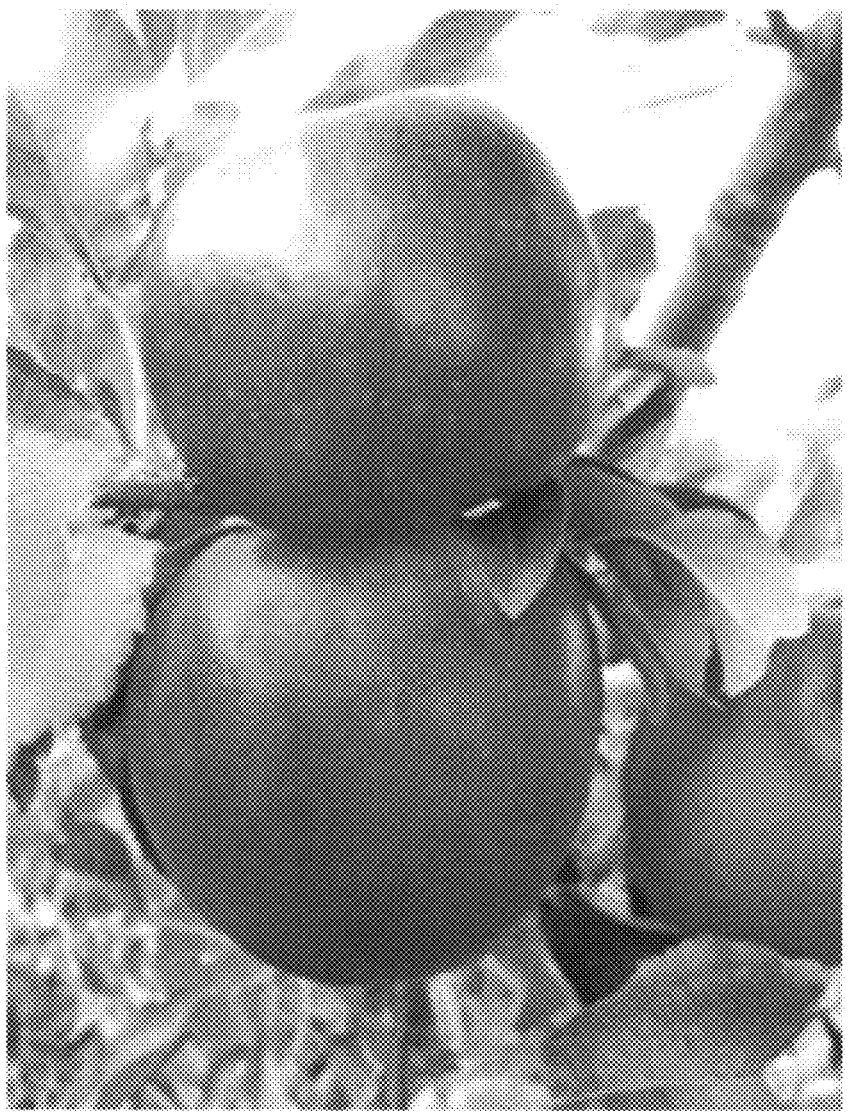

FIG. 3. Photograph of a fully developed fruit, close-up, on a tree grown in an orchard, showing the color development and shape of the fruit of this new variety

DETAILED BOTANICAL DESCRIPTION

The photographs and botanical description are taken from trees grown in the Koue-Bokkeveld region near Ceres in the Western Cape, South Africa. The farm is situated in a main apple growing area and general commercial orchard practices are applied to the trees. The climate is temperate continental with low temperatures during winter and high temperatures during summer. The soil type is sandy rock with a micro-jet irrigation system. The photographs and description are believed to apply to plants of the variety grown elsewhere under similar soil and climate conditions.

The detailed botanical description is taken from over two fruiting seasons of trees budded on a standard apple rootstock. The trees were five years old when the first observations were made. Measurements and numerical values represent averages for typical plants and plant parts. The actual measurements of any individual plant or plant part, or any group of plants or plant parts, may vary from the stated average. Reference to colors are based on The Royal Horticultural Society Color Chart, 5th Edition, 2007.

Plant description:

*Plant and growth habit.*—Trees have a spreading growth habit reaching a height of 3 m and spread of 1.5 m. Trees were planted at a distance of 4 by 1.5 m.

*Bearing on both spurs and long shoots.*

*Tree type.*—Ramified.

*One-year-old shoot.*—Shoot thickness: Medium, 50-58 mm. Length of internodes: Long, 33-37 mm. Color on sunny side: Dark Brown (166A). Pubescence: Present. Number of lenticels: Present, medium; 30 per 5 cm shoots with a shoot thickness of 5 mm. The shape of the lenticels is oval; the height is 1.3 mm; the width is 1.1 mm; and the color is 116D.

*Trunk description.*—Diameter: 54-64 mm (10 cm above the soil). Texture: Woody. Color: 174B.

*Branch description.*—Length: 80-100 cm. Diameter: 22-24 mm. Internode: 50-70 mm. Texture: Smooth. Color: 177B. Angle of attachment: 40-60 from horizontal. Branch habit: Spreading — Angle of attachment 40-60° from horizontal.

*Leaf description.*—Leaf arrangement: Single, alternate, spiral. Leaf attitude: Upwards to outwards in relation to the shoot. Length: Medium length, 97-105 mm. Width: Narrow width, 50-52 mm. Length width ratio: Large, 1.9-2.1. Shape: Elliptical. Apex: Acuminate. Base: Wedge-shaped. Margin: Serrate to slightly bi-serrate. Texture upper surface: Smooth. Texture lower surface: Woolly, rough, pubescent. Venation pattern: Pinnate to reticulate towards leaf edge. Color for developing and fully-developed leaves upper surface: N137C. Color for developing and full developed leaves upper surface: Venation pattern — 145B. Color for developing and full developed leaves lower surface: 146B. Color for developing and full developed leaves lower surface: Venation pattern — 149D. Pubescence: Present, Medium on the lower side. Petiole extent of anthocyanin coloration from the base: Small-medium; Quarter of the petiole length; Anthocyanin color, N74B. Petiole length: Medium, 33-37 mm. Petiole diameter: 1.5-1.9 mm. Texture upper surface: Slightly woolly. Texture lower surface: Smooth. Petiole color: Upper surface, 143B. Petiole color: Lower surface, 149D.

*Stipule.*—Number: 2. Shape: Elongated, pointed. Length: 5.5-7.8 mm. Width: 0.7-1.2 mm. Color: 139C green group.

Flower description:

*Flower type and flowering habit.*—Small flower with medium pink color when unopened; flowers arranged in clusters, facing outward.

*Fragrance.*—Slight, honey.

*Natural flowering season.*—Beginning of flowering: Medium, 3$^{rd}$ to 4$^{th}$ week of September (Koue Bokkeveld, Ceres).

*Inflorescence height.*—37-42 mm.

*Inflorescence diameter.*—54-58 mm.

*Quantity of flowers per inflorescence.*—Mostly 5, in 10% of clusters.

*Flower diameter.*—32-42 mm.

*Flower depth (height).*—14-16 mm.

*Flower longevity on plant.*—6-8 days.

*Buds.*—Shape: Oval, elongated. Length: 9-11 mm just before opening. Diameter: 8-10 mm just before opening. Color: white (NN155D) with pink (N74B, 30-50%).

*Petals.*—Intermediate arrangement of petals, mostly free. Quantity of petals: 5. Petal length: 18 mm. Petal width: 10-11 mm. Petal shape: Oblong — obovate. Petal apex: Rounded. Petal base: Wedge-shaped. Petal margin: Smooth, entire. Petal texture upper: Smooth, satiny. Petal texture lower side: Smooth. Petal color upper: 115D. Petal color lower: 155D with red — N74B (20-30% pink, mainly veins).

*Sepals.*—Quantity: 5. Arrangement: Free, curled. Length: 6-7 mm. Width: 3-4 mm. Shape: Elliptical. Apex: Acuminate (slight red). Base: Truncate. Texture: Hairy, with pubescence on upper and lower side. Color: 193B On upper and lower side. Margin: Entire with pubescence.

*Pedicels.*—Length: 13-155 mm. Diameter: 1.3-1.8 mm. Strength: Moderately strong. Aspect: 45-90° from stem. Texture: Hairy. Color: Green 146C (tinged with red 177B). Reproductive organs: Stamens quantity: 11-18 per flower. Filament length: 5-7 mm. Anther length: 1.9-2.5 mm. Anther shape: bi-lobed, oblong. Anther color: 1D-1C. Pollen amount: Average — scarce. Pollen color: 160A (dried). Pistils quantity: 5. Pistil length: 9.5-11 mm. Stigma color: 150C. Style length: 7.5-8.5 mm. Style color: 145C. Ovary length: 5.6 mm. Ovary color: 143A.

*The tree is Scab Resistant (Vf-gene) and susceptible to Mildew.*

Fruit description:

*Ripening time*.—Typically early, End of February, in South Africa, after Gala.

*Yield*.—Moderate, 50 kg per tree.

*Use*.—Fresh.

*Fruit*.—Length/height: Long, 61-63 mm. Diameter: Medium, 66-72 mm. Weight: ±170 g. Shape: Ovoid. Depth of eye basin: Medium, 11-12 mm. Width of eye basin: Narrow, 22 mm.

*Fruit stalk*.—Diameter: Medium, 3.6-41. mm. Color: Green 151A. Length: 15 mm. Thickness: 3.6-4.1 mm. Stalk and cavity depth: 10-14 mm. Stalk cavity diameter: 22 mm.

*Fruit skin*.—Color: Yellow ground color, 2C. Over color: Dark red, 187B on sunny side, 46A background of fruit; degree of over-color: 60-100%. Solid flush with weak stripes and medium width of stripes. Absent or small area of fruit russet around stalk attachment, on cheeks or around eye basin.

*Lenticels*.—Number: Slightly prominent, 4-7 lenticels/$cm^2$. Size of lenticels: length, 1.2 mm; width, 1 mm. Color of lenticels: White 155C.

*Flesh texture*.—Crisp, firm.

*Flesh color*.—Cream pinkish 11D with red coloration under skin 185B.

*Locules*.—Number per locule: 1-2. Length: 8-10 mm. Width: 6-7 mm. Shape: Fully open in cross section aperture.

*Seeds*.—Quantity: Ranging from 2 to 8 per fruit depending on environmental conditions. Length: 10-12 mm. Width: 4.8-5.8 mm. Diameter: 2.5-3.3 mm. Shape: Elliptical, asymmetrical. Color: Brown, 166B.

*Fruit retains good quality during shipping for a period of* 8 *weeks at* 1° *C.*

What is claimed is:

1. A new and distinct variety of apple tree having the characteristics substantially as described and illustrated herein.

* * * * *